United States Patent
McEvoy et al.

(10) Patent No.: US 11,813,417 B2
(45) Date of Patent: Nov. 14, 2023

(54) CATHETER MODIFICATION DEVICE

(71) Applicant: Medtronic Vascular, Inc., Santa Rosa, CA (US)

(72) Inventors: Francis Denis McEvoy, Laois (IE); Colm Connolly, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 821 days.

(21) Appl. No.: 16/539,636

(22) Filed: Aug. 13, 2019

(65) Prior Publication Data
US 2021/0046289 A1    Feb. 18, 2021

(51) Int. Cl.
| | |
|---|---|
| *A61M 25/09* | (2006.01) |
| *A61M 25/01* | (2006.01) |
| *A61M 25/10* | (2013.01) |
| *A61F 2/966* | (2013.01) |
| *A61M 25/00* | (2006.01) |

(52) U.S. Cl.
CPC .... *A61M 25/0905* (2013.01); *A61M 25/0009* (2013.01); *A61M 25/0102* (2013.01); *A61M 25/09041* (2013.01); *A61M 25/10* (2013.01); *A61F 2/966* (2013.01)

(58) Field of Classification Search
CPC .......... A61M 25/0905; A61M 25/0009; A61M 25/0102; A61M 25/09041; A61M 25/10; A61M 25/0662; A61M 25/001; A61M 2025/0175; A61F 2/966; B29L 2031/7542; B29L 2031/7548; B29C 57/04; B29C 57/045; B29C 57/06

See application file for complete search history.

(56) References Cited

U.S. PATENT DOCUMENTS

| | | | |
|---|---|---|---|
| 3,554,580 A | | 1/1971 | Goyke |
| 3,732,054 A | * | 5/1973 | Lyng ................ B29C 57/04 425/469 |
| 3,899,280 A | * | 8/1975 | Bailey .............. B29C 57/04 65/282 |

(Continued)

FOREIGN PATENT DOCUMENTS

| | | | | |
|---|---|---|---|---|
| AT | 187232 B | * | 12/1955 | ............ B29C 57/00 |
| CN | 106345039 A | | 1/2017 | |

(Continued)

OTHER PUBLICATIONS

Kumar et al., "The GuideLiner "Child" Catheter for Percutaneous Coronary Intervention—Early Clinical Experience", Cath Lab Digest, vol. 19, Issue 3, Mar. 2011, 14 pp.

(Continued)

*Primary Examiner* — Katherine H Schwiker
*Assistant Examiner* — Adam J. Cermak
(74) *Attorney, Agent, or Firm* — Shumaker & Sieffert, P.A.

(57) ABSTRACT

In some examples, a catheter flaring device includes a housing and a pin. The housing includes an interior surface defining a cavity configured to receive at least a portion of a catheter having an entry port and engage an exterior surface of the catheter proximate the entry port. The pin is configured to be advanced into the entry port of the catheter to increase a cross-sectional dimension of the entry port. Flaring the entry port may help reduce catching of a medical device on the entry port of the catheter during a medical procedure.

22 Claims, 9 Drawing Sheets

(56) References Cited

U.S. PATENT DOCUMENTS

| | | | |
|---|---|---|---|
| 4,009,982 A * | 3/1977 | Maier | B29C 53/083 |
| | | | 425/389 |
| 4,404,159 A * | 9/1983 | McFarlane | A61M 25/001 |
| | | | 264/296 |
| 4,430,052 A * | 2/1984 | Olsson | B29C 57/04 |
| | | | 425/392 |
| 5,102,324 A * | 4/1992 | Bullard | B29C 57/00 |
| | | | 425/150 |
| 5,117,839 A | 6/1992 | Dance | |
| 5,135,599 A | 8/1992 | Martin et al. | |
| 5,385,562 A | 1/1995 | Adams et al. | |
| 5,843,051 A | 12/1998 | Adams et al. | |
| 5,935,114 A | 8/1999 | Jang et al. | |
| 6,156,054 A | 12/2000 | Zadno-Azizi et al. | |
| 6,663,597 B1 | 12/2003 | Windheuser et al. | |
| 6,860,524 B1 * | 3/2005 | Rowley | B29C 57/00 |
| | | | 285/332 |
| 7,322,988 B2 | 1/2008 | Sterud et al. | |
| 7,604,472 B2 * | 10/2009 | Hayes, Jr. | B29B 13/025 |
| | | | 425/384 |
| 7,704,067 B2 * | 4/2010 | Adams | B29C 43/36 |
| | | | 425/383 |
| 7,708,744 B2 * | 5/2010 | Soma | A61M 25/09 |
| | | | 606/108 |
| 8,292,850 B2 | 10/2012 | Root et al. | |
| 9,144,662 B2 * | 9/2015 | Di Caprio | A61M 25/0068 |
| 9,179,919 B2 | 11/2015 | Webler et al. | |
| 9,545,750 B2 * | 1/2017 | Hayes, Jr. | B29C 57/04 |
| 9,868,238 B1 * | 1/2018 | Scopton | B29B 13/08 |
| 9,987,672 B2 * | 6/2018 | Houle | B21D 41/02 |
| 10,124,146 B2 | 11/2018 | Di Caprio et al. | |
| 10,729,884 B2 * | 8/2020 | Connolly | A61M 25/0102 |
| 2004/0140585 A1 * | 7/2004 | Sterud | A61M 25/008 |
| | | | 264/248 |
| 2004/0144485 A1 * | 7/2004 | Dojan | A43B 13/203 |
| | | | 156/304.2 |
| 2005/0005987 A1 * | 1/2005 | Hayes | B29C 57/04 |
| | | | 425/393 |
| 2006/0144982 A1 * | 7/2006 | Fernandez-Sein | B29C 63/18 |
| | | | 242/364 |
| 2007/0006441 A1 * | 1/2007 | McNiven | A61F 2/958 |
| | | | 29/508 |
| 2007/0250150 A1 * | 10/2007 | Pal | A61F 2/2436 |
| | | | 606/108 |
| 2008/0150194 A1 * | 6/2008 | Thomas | A61M 25/001 |
| | | | 264/320 |
| 2010/0280498 A1 * | 11/2010 | Olsen | A61M 25/0015 |
| | | | 83/16 |
| 2013/0305803 A1 * | 11/2013 | Wiget | B21D 41/00 |
| | | | 72/453.01 |
| 2014/0052097 A1 * | 2/2014 | Petersen | A61M 25/0069 |
| | | | 604/528 |
| 2014/0276618 A1 * | 9/2014 | Di Caprio | A61M 25/0069 |
| | | | 604/528 |
| 2016/0045708 A1 * | 2/2016 | Westhoff | A61M 39/10 |
| | | | 604/533 |
| 2016/0136718 A1 * | 5/2016 | Lee | B29C 57/04 |
| | | | 425/392 |
| 2016/0167102 A1 * | 6/2016 | Norris | B29C 57/045 |
| | | | 72/460 |
| 2016/0346502 A1 * | 12/2016 | Fuller | A61M 25/04 |
| 2017/0232838 A1 * | 8/2017 | Fukuyasu | B32B 27/08 |
| | | | 220/86.2 |
| 2017/0239447 A1 * | 8/2017 | Yang | A61M 25/0009 |
| 2017/0333675 A1 * | 11/2017 | Cottone | A61M 25/0023 |
| 2017/0354800 A1 * | 12/2017 | O'Donovan | A61M 25/0043 |
| 2018/0161547 A1 * | 6/2018 | Brenizer | A61M 25/0113 |
| 2018/0297268 A1 * | 10/2018 | Edward | B29C 63/06 |
| 2018/0319074 A1 * | 11/2018 | Lyons | B29C 57/04 |
| 2018/0353728 A1 * | 12/2018 | Di Caprio | A61M 25/0102 |
| 2020/0061902 A1 * | 2/2020 | Liu | B21D 41/028 |
| 2020/0353209 A1 * | 11/2020 | Westhoff | B29C 65/1635 |
| 2022/0192703 A1 * | 6/2022 | O'Connell | A61B 17/3423 |

FOREIGN PATENT DOCUMENTS

| | | | | |
|---|---|---|---|---|
| CN | 108790137 A | * | 11/2018 | |
| CN | 113232319 A | * | 8/2021 | |
| DE | 19601993 A1 | * | 10/1996 | B29C 57/04 |
| DE | 20305730 U1 | * | 9/2003 | |
| EP | 2797656 B1 | * | 7/2020 | |
| GB | 744327 A | * | 2/1956 | |
| GB | 744327 A | | 2/1956 | |
| JP | 54016577 A | * | 2/1979 | B29C 57/04 |
| JP | 54036384 A | * | 3/1979 | |
| KR | 100562163 B1 | * | 3/2006 | F16L 9/127 |
| WO | WO-2019021554 A1 | * | 1/2019 | |

OTHER PUBLICATIONS

International Search Report and Written Opinion of International Application No. PCT/US2020/045559, dated Nov. 26, 2020, 15 pp.

* cited by examiner

CATHETER MODIFICATION DEVICE

TECHNICAL FIELD

This disclosure relates to medical devices.

BACKGROUND

A medical catheter may be use with various medical procedures. For example, in some cases, a medical catheter may be used to deliver a medical device and/or composition within vasculature of a patient.

SUMMARY

Example devices, systems, and techniques described herein may be used to increase a cross-sectional dimension (e.g., a diameter in the case of a circular cross-section) of an entry port into a lumen of a catheter. In some examples, the entry port may be at a proximal end of a catheter, while in other examples, such as in the case of a guide extension catheter, the entry port may be distal to the proximal end of the catheter. Increasing an outer cross-sectional dimension of the entry port, referred to herein as "flaring" of the entry port, may widen the entry port without increasing the outer cross-sectional diameter of other portions of the catheter (e.g., a distal portion), which may facilitate the introduction of medical devices into the catheter lumen without adversely impacting the navigability of the catheter through vasculature of a patient. In some examples, a flaring device having a pin is configured to be advanced into an entry port of a catheter to increase a cross-sectional dimension of at least a portion of the entry port. Flaring the entry port may reduce catching of a medical device on the entry port, which may facilitate medical procedures using an inner catheter defining an outer diameter and an outer catheter defining an inner diameter that is larger than the outer diameter of the inner catheter.

In some examples, the disclosure describes a device including a housing and a pin. The housing includes an interior surface defining a cavity configured to receive at least a portion of a catheter having an entry port. The interior surface of the housing is configured to engage an exterior surface of the catheter proximate the entry port. The pin is configured to be advanced into the entry port of the catheter while at least the portion of the catheter is positioned in the cavity to increase a cross-sectional dimension of the entry port.

In some examples, the disclosure describes a medical device system that includes a catheter and a flaring device. The catheter includes an elongate body extending along a central longitudinal axis and defining a lumen terminating in an entry port. The flaring device includes a housing and a pin. The housing includes an interior surface defining a cavity shaped to receive at least a portion of the catheter. The interior surface of the housing is configured to engage an exterior surface of the catheter proximate the entry port. The pin is configured to be advanced into the entry port of the catheter while at least the portion of the catheter is positioned in the cavity to flare the entry port to define a flared lip extending away from the central longitudinal axis.

In some examples, the disclosure describes a method that includes positioning at least an entry port of a catheter in a cavity of a housing of a flaring device. The catheter includes an elongate body extending along a central longitudinal axis and defining a lumen terminating in the entry port. the flaring device includes a housing and a pin. The housing includes an interior surface defining the cavity shaped to receive at least a portion of the catheter comprising the entry port. The interior surface of the housing is configured to engage an exterior surface of the catheter proximate the entry port. The method also includes, while at least the entry port of the catheter is positioned in the cavity of the housing, advancing the pin into the entry port of the catheter to flare the entry port to increase a cross-sectional dimension of the entry port.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
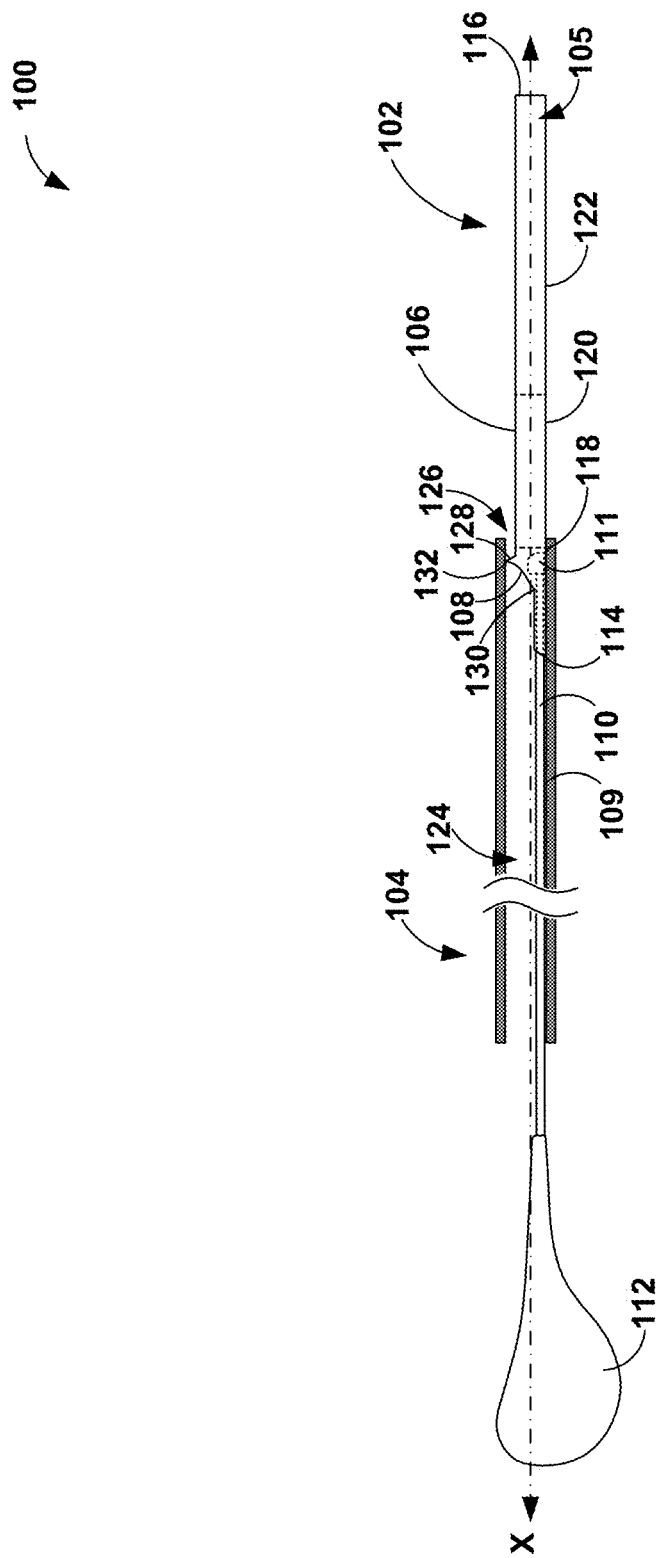
FIG. 1 is a conceptual side view of an example medical device system that includes a catheter and an outer catheter, which is shown in cross-section.

In some examples, a flaring device including a pin is configured to modify an entry port to a lumen of a catheter, such as by increasing a cross-sectional dimension of the entry port. As discussed in further detail below, increasing a cross-sectional dimension of the entry port, referred to herein as "flaring" of the entry port, may widen the entry port without increasing the outer cross-sectional diameter of other portions of the catheter (e.g., a distal portion), which may facilitate the introduction of medical devices into the catheter lumen without adversely impacting the navigability of the catheter through vasculature of a patient.

The pin of the flaring device is configured to be advanced into an entry port of a catheter and increase a cross-sectional dimension of at least a portion of the entry port, such as by causing the catheter wall defining the entry port to change size and/or shape. For example, advancing the pin into the entry port a selected distance may flare at least a portion of the entry port in a radial direction. The flared portion of the entry point defines a flared lip of the catheter. The flared lip may include at least one of a selected orientation relative to the entry port, a selected cross-sectional dimension (e.g., diameter or width), a selected length from the entry port to a non-flared portion of the catheter, or may extend along an arc that subtends a selected angle of the outer perimeter of the entry port. In some examples, flaring the entry port may facilitate the introduction of medical devices into the catheter lumen without adversely impacting the navigability of the catheter through vasculature of a patient. By flaring the entry port, the entry port into the catheter lumen may better correspond to an inner diameter of a second catheter in which the catheter is positioned, for example, compared to an unflared catheter. Although the second catheter is primarily referred to as an outer catheter or a guide catheter herein, the second catheter may be any suitable type of catheter.

In some examples, the catheter may include a guide extension catheter including a push assembly and an elongate body having a distal end and a proximal entry port. Guide extension catheters ("GECs") may include rapid exchange percutaneous intervention (PCI) devices. The elongate body of a GEC defines at least one lumen through which a medical device (e.g., a catheter, guidewire, filter, stent delivery system, and the like), therapeutic agent, or other element can be introduced into vasculature or other tissue sites of a patient. The elongate body may be coupled to the push assembly, which has a lower profile than the elongate body and facilitates pushability of the GEC through an outer catheter and/or through vasculature of a patient. In some examples, the push assembly may include an elongate member and an anchor member positioned at a distal end of the elongate member.

A GEC may be better suited for navigation through such heavy tortuosity and/or calcification than an outer catheter (e.g., a guide catheter) due to its flexibility and lower profile. In some examples, a clinician may push the GEC out of a distal end of the outer catheter upon the approach of the outer catheter to such a region that would be difficult or impossible for the outer catheter to extend through. In some examples, the GEC may be said to "telescope" out of the outer catheter when it is pushed out of a distal end of the outer catheter. In some examples, the GEC may provide additional back up support for delivery of medical devices, therapeutic agents, or other elements introduced into vasculature or other tissue sites of a patient via the outer catheter.

In some cases, a clinician may select an outer catheter having a particular outer diameter (and a corresponding inner diameter) and a GEC having a smaller outer diameter than the inner diameter of the outer catheter. The clinician may select the smaller diameter GEC to enable the GEC to be introduced into an inner lumen of the outer catheter. In addition, the clinician may select a smaller outer diameter GEC to enable the GEC to be navigated to relatively difficult to reach target sites. The smaller outer diameter GEC may provide, for example, improved deliverability and/or dimensional advantage when navigating vasculature of a patient compared to a larger outer diameter outer catheter or a larger outer diameter GEC. As one example, a clinician may use a guide catheter having an inner diameter of 7 Fr and a GEC having an outer diameter of 5 Fr. As another example, a clinician may use a guide catheter having an outer diameter of 7 Fr and a 7 Fr GEC, which may be designated as such because it is configured to be received in an inner lumen of the 7 Fr guide catheter, but in actuality has an outer diameter that is smaller than 7 Fr, e.g., about 0.3 mm smaller than 7 Fr. This difference in the outer diameter of the GEC and the inner diameter of an outer catheter may be referred to as a GEC-mismatch.

During delivery of the selected medical device via the GEC and the outer catheter, the GEC-mismatch may cause a portion of the medical device to catch at the entry port of the GEC. For example, a tip or other leading portion of the medical device positioned in an outer catheter lumen of the outer catheter and being guided into the GEC lumen may catch on the entry port of the GEC. As a result, additional force may be necessary to force the medical device into the GEC lumen via the entry port and/or a clinician may need to take additional time to try to introduce the medical device into the GEC lumen via the entry port, such as by withdrawing the medical device relative to the GEC entry port and realigning the medical device with the GEC entry port. The tip or other leading portion of the medical device can include, for example, a distal end of a catheter, a leading strut of a stent, a radiofluorescent marker band, a leading edge of an inflatable balloon, or other feature of the medical device. To reduce catching of the medical device on the entry port of the GEC, the flaring device, systems, and techniques describe herein may be used to modify the entry port of the GEC to better match the outer diameter of the GEC to the inner diameter of the guide catheter. In this way, the described flaring device, systems, and techniques may reduce the above described inconveniences associated with GEC-mismatch.

FIG. 1 is a conceptual side view of an example medical device system 100 that includes catheter 102 and an outer catheter 104. Catheter 102 includes an elongate body 106 having an entry port 108, a push assembly 110, and a handle 112. In some examples, catheter 102 may include a GEC.

Catheter 102 defines a longitudinal axis X, which is shown as a central longitudinal axis of elongate body 106 in FIG. 1. In some examples, push assembly 110 may include an elongate member 109 and an anchor member 111. Anchor member 111 may be positioned at a distal portion of elongate member 109 and fixed to a proximal portion of elongate body 106 proximate entry port 108. For example, anchor member 111 may extend between material layers forming elongate body 106, may be adhered to a portion of elongate body 106, or both. Elongate body 106 defines a proximal end 114 and a distal end 116. In some examples, a maximum cross-sectional dimension of elongate body 106 between proximal end 114 and a distal end 116 may be less than a cross-sectional dimension of entry port 108. Elongate body 106 is configured to provide a delivery member on catheter 102 that may extend distally of outer catheter 104 to telescope out of a distal end of outer catheter 104 and effectively extend a reach of outer catheter 104 within vasculature of a patient. Extending the reach of outer catheter 104 may enable delivery of devices, agents, and/or any other suitable elements to target sites that may be difficult to reach with outer catheter 104.

In some examples, elongate body 106 includes a tapered portion 118, a proximal portion 120, and a distal portion 122. Tapered portion 118, proximal portion 120, and distal portion 122 may be integrally formed or separate members adhered, or otherwise joined, together. Tapered portion 118 of elongate body 106 is tapered towards central longitudinal axis X in a proximal direction. The tapering of elongate body 106 at tapered portion 118 may enable elongate body 106 to more easily be retracted into outer catheter 104. For example, during or after use of catheter 102, a clinician may desire to retract at least a portion of elongate body 106 within outer catheter 104 by retracting push assembly 110 proximally with respect to outer catheter 104. Tapered portion 118 may enable smoother entry of elongate body 106 into outer catheter 104.

Proximal portion 120 and distal portion 122 may have similar or different stiffness. For example, distal portion 122 may have a stiffness that is greater than a stiffness of the proximal portion 120. In other examples, distal portion 122 may have a stiffness that is less than proximal portion 120. A stiffer proximal portion 120 may help maintain the integrity of the proximal portion of lumen 105 of elongate body 106, which may aid in introduction of medical devices into lumen 105 from entry port 108 without adversely impacting the navigability of catheter 102 through vasculature of a patient. For example, a stiffer proximal portion 120 may help entry port 108 and a proximal-most portion of elongate body 106 resist deformation to help maintain lumenal integrity. In some examples, proximal portion 120 may be approximately 1 centimeter (cm) to approximately 4 cm long, such as approximately 2.5 cm long or approximately 1.25 cm long. In some examples, distal portion 122 may be approximately 15 cm to approximately 27 cm long, such as approximately 24 cm long to approximately 26 cm long, or approximately 25 cm long. The lengths may be measured along longitudinal axis X.

Outer catheter 104 defines an outer catheter lumen 124, through which catheter 102 may be introduced in order to access, for example, a distal target site within vasculature of a patient. Thus, at least a portion of outer catheter 104 may be configured to surround catheter 102. In some examples, outer catheter 104 may include a guide catheter. Outer catheter 104 may further define distal opening 126 and, in some examples, at least a portion of catheter 102 may be configured to extend through distal opening 126 and distally of outer catheter 104. For example, at least a part of elongate body 106 of catheter 102 may be configured to extend out of distal opening 126 of outer catheter 104 to extend through heavy tortuosity or calcification within a body vessel. Catheter 102 may have a smaller radial profile and may be more flexible than outer catheter 104 such that it may more easily navigate through heavy tortuosity or calcification within a body vessel than outer catheter 104.

In some examples, to enable catheter 102 to be introduced into outer catheter lumen 124 and slide within outer catheter lumen 124, a maximum cross-sectional dimension (e.g., an outer perimeter or outer radial profile) of elongate body 106 of catheter 102 may be smaller or shaped differently than a maximum cross-sectional dimension of an inner perimeter (e.g., an inner radial profile) of outer catheter 104. In other words, an outer perimeter of catheter 102 may be mismatched with an inner perimeter of catheter 104. For example, in the case of catheters 102, 104 having circular cross-sections, an inner diameter of catheter 104 (defining lumen 124) may be larger than an outer diameter of elongate body 106. Lip 128 of entry port 108 of elongate body 106 is configured to reduce the mismatch of the outer perimeter of catheter 102 with the inner perimeter of catheter 104. For example, as discussed below, lip 128 may be a flared lip that flares radially outward relative to central longitudinal axis X to reduce a space between entry port 108 and the walls of outer catheter 104 defining lumen 124.

Entry port 108 may extend from a proximal end 130 to a distal end 132 along a length of elongate body 106 (the length being measured along longitudinal axis X). In some examples, entry port 108 may be angled from distal end 132 to proximal end 130 due to the tapered shape of tapered portion 118 of elongate body 106. Entry port 108 may include a substantially straight or curvilinear edges. In some examples, entry port 108 may be formed by skiving at least part of portion 118 of elongate body 106. In some examples, entry port 108 may have a length, measured from proximal end 130 to distal end 132 along longitudinal axis X, of about 2 centimeters (cm) to about 10 cm (e.g., 2 cm to 10 cm or nearly 2 cm to 10 cm, to the extent permitted by manufacturing tolerances), such as about 3.5 cm to about 4.5 cm or about 4 cm. It is believed that a tapered entry port 108 having a relatively longer length and being angled from distal end 132 to proximal end 130 may help contribute to smooth delivery of a medical device (e.g., an interventional medical device) into lumen 105 of elongate body 106 via entry port 108 by guiding the medical device into lumen 105.

Figure 3A:
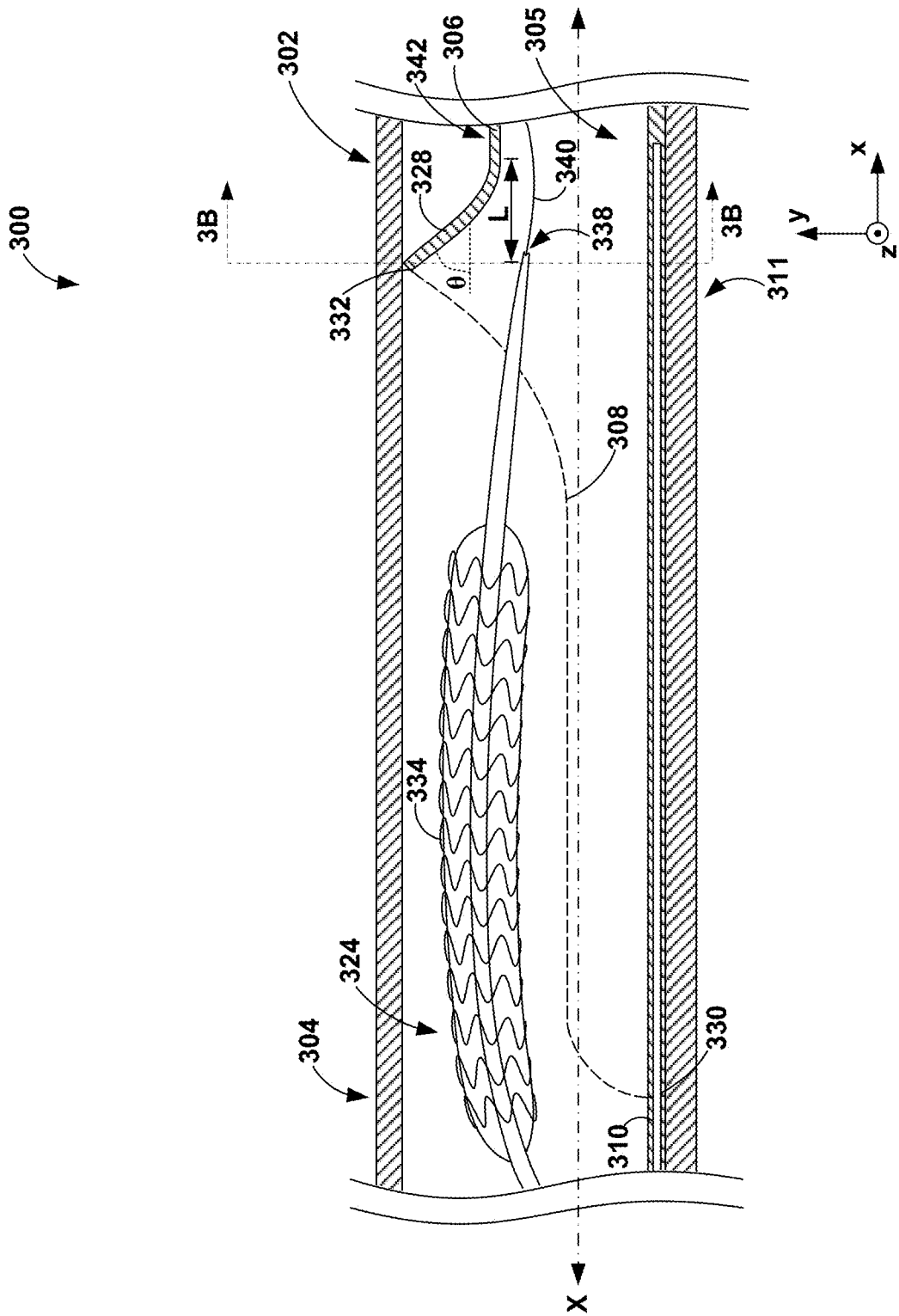
FIG. 3A is a conceptual longitudinal cross-sectional view of an example medical device system illustrating a flared entry port of a modified catheter positioned within a lumen of an outer catheter and into which a medical device is being inserted.

Lip 128 is configured to increase a cross-sectional dimension of the outer perimeter of entry port 108. Generally, lip 128 may include any suitable shape or size that enables an outer perimeter of elongate body 106 at lip 128 to more closely match an inner perimeter of catheter 104. In some examples, lip 128 is asymmetrical relative to central longitudinal axis X. In some examples, an angle of lip 128 relative to central longitudinal axis X is greater than 0 to about 45 degrees (e.g., angle θ as illustrated in FIG. 3A). In some examples, a length of lip 128 in a direction parallel to longitudinal axis X is about 3 millimeters (mm) to about 5 mm. In some examples, an outer perimeter of lip 128 may subtend an angle from about 45-degrees to about 315-degrees. The shape and/or size of lip 128 may be selected to define a relatively smooth transition between elongate body 106 and outer catheter 104, e.g., when only a portion of elongate body 106 extends distally of distal opening 126 of outer catheter 104 and another portion remains within lumen 124 of outer catheter 104 and/or when a proximal end of elongate body 106 abuts a distal end of outer catheter 104. Additionally, or alternatively, lip 128 may provide a relatively snug fit inside of outer catheter 104 when elongate body 106 is at least partially within outer catheter 104.

In some examples, the relatively smooth transition and/or snug fit between lip 128 and an inner surface of outer catheter 104 may provide certain advantages. For example, medical devices and/or other elements may be easier to advance from lumen 124 of outer catheter 104 to lumen 105 of elongate body 106 because the transition between lumen 124 and lumen 105 may be relatively smooth such that components being delivered may not get caught at entry port 108 and/or the transition from lumen 124 to lumen 105. As an additional example, lip 128 may reduce the leakage of fluids out of distal opening 126 of outer catheter 104 when the fluid is being delivered through outer catheter lumen 124 into elongate body lumen 105. In some examples, flaring entry port 108 may facilitate the introduction of medical devices into the catheter lumen without adversely impacting the navigability of catheter 102 through vasculature of a patient Although entry port 108 of elongate body 106 is illustrated as being positioned within lumen 124 of outer catheter 104, such that an interventional medical device or another medical device can be introduced from lumen 124 of outer catheter 104 into lumen 105 of elongate body 106 without exiting lumen 124, in other examples catheter 102 may extend out distal opening 126 of outer catheter 104 such that proximal end 114 of elongate body 106 is distal to distal opening 126

Figure 2A:
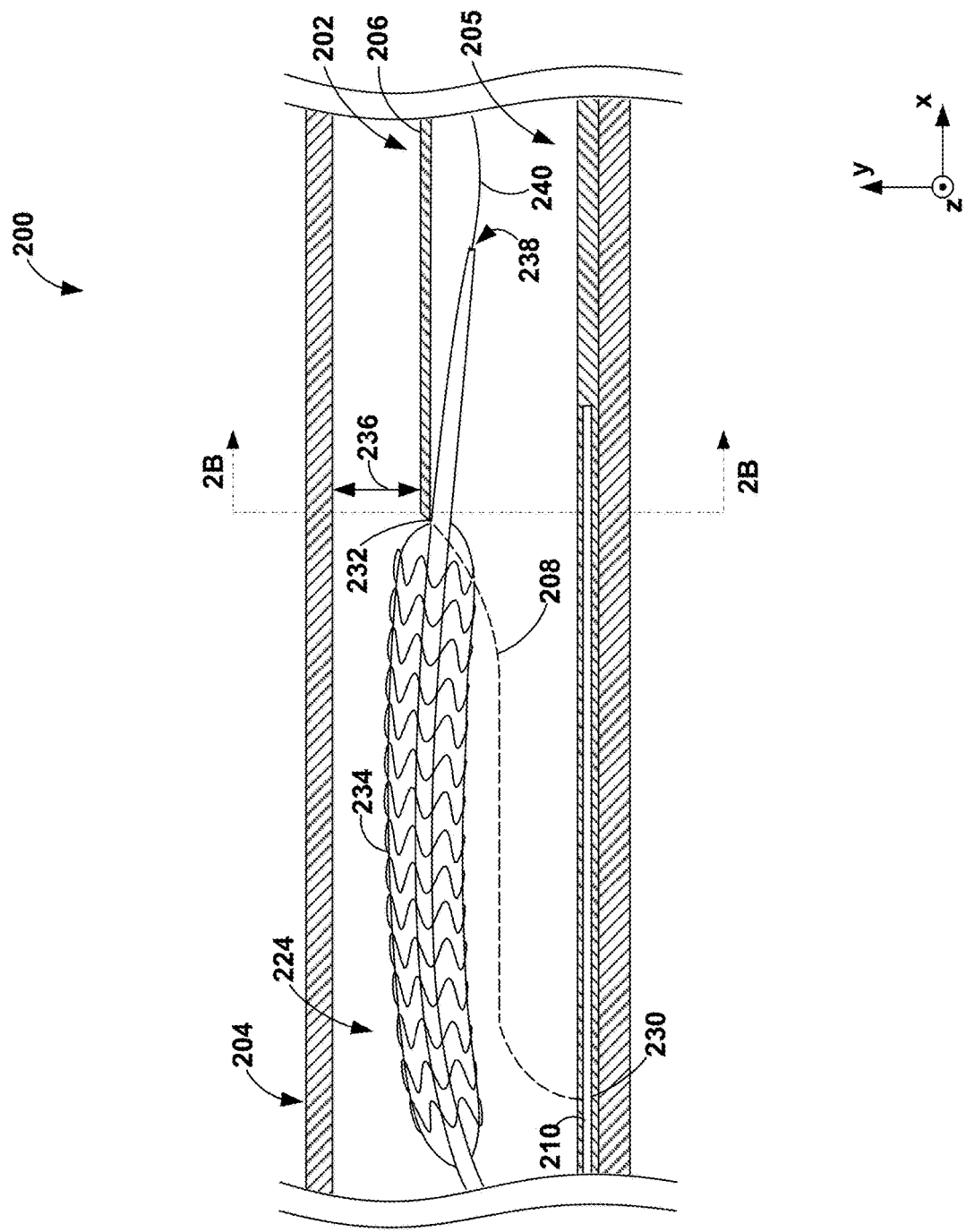
FIG. 2A is a conceptual longitudinal cross-sectional view of an example medical device system illustrating the entry port of a catheter positioned within a lumen of an outer catheter and into which a medical device is being inserted.
Figure 2B:
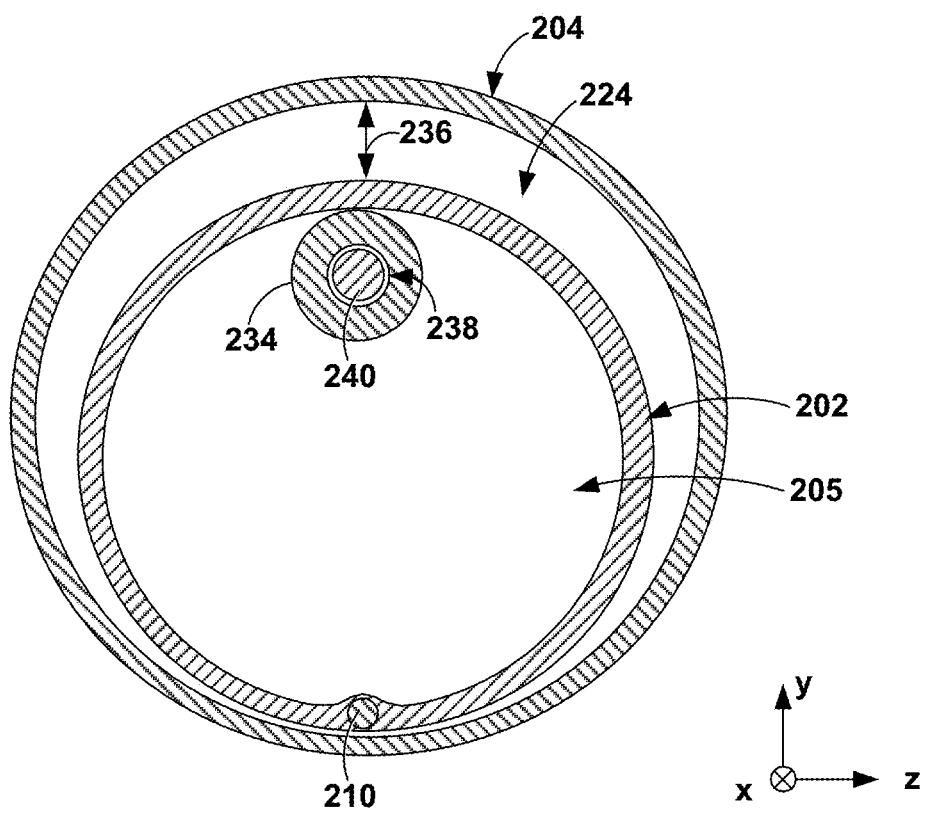
FIG. 2B is a conceptual transverse cross-sectional view of the example medical device system illustrated in FIG. 2A taken along line 2B-2B in FIG. 3A.

FIG. 2A is a conceptual longitudinal cross-sectional view of an example medical device system 200 illustrating an entry port 208 of a catheter 202 positioned within a lumen 224 of an outer catheter 204 and into which a medical device 234 is being inserted. FIG. 2B is a conceptual transverse cross-sectional view of the example medical device system 200 illustrated in FIG. 2A. Catheter 202 and outer catheter 204 may be the same as or substantially similar to catheter 102 and outer catheter 104, respectively, as discussed above in reference to FIG. 1, except for the differences described herein. For example, catheter 202 includes a push assembly 210 coupled to an elongate body 206. Elongate body 206 extends along a longitudinal axis and defines an entry port 208 into a lumen 205. Entry port 208 extends from proximal end 230 to distal end 232 along a length of elongate body 206. Also, outer catheter 204 defines a lumen 224 through which catheter 202 may pass.

As illustrated in FIG. 2A, entry port 208 does not include a lip, and catheter 202 and outer catheter 204 define a mismatch 236. As discussed above, mismatch 236 may include the difference between an outer diameter of catheter 202 and an inner diameter of outer catheter 204. Although discussed as a difference in diameter, in other examples the difference may be with respect to another cross-sectional dimension or shape of catheter 202 and outer catheter 204. In some examples, mismatch 236 may be from about 0.33 mm to about 2 mm, such as about 0.5 mm to about 1 mm. Although mismatch 236 is illustrated as a gap extending within lumen 224 between an upper surface of elongate body 206 of catheter 202 and an interior surface of catheter 204, in some examples, mismatch 236 may include a gap extending around any portion of the outer perimeter of elongate body 206.

In some examples, when medical device 234 is guided from lumen 224 of outer catheter 204 toward catheter 202, mismatch 236 may cause at least a portion of medical device 234 to catch on entry port 208. Medical device 234 may include any suitable medical device, such as, but not limited to, a catheter, guidewire, filter, stent delivery system, therapeutic agent delivery devices, or other elements introduced into vasculature or other tissue sites of a patient. In some cases, medical device 234 may include a lumen 238 (FIG. 2B) such that medical device 234 may be advanced over a guidewire 240. When a leading edge of medical device 234 contacts entry port 208, mismatch 236 may cause a portion of medical device 234 to catch at entry port 208. For example, a leading strut of a stent of medical device 234 may protrude in the radial direction such that medical device 234 may catch on entry port 208. In some examples, a clinician may not be able to apply sufficient push force to urge medical device 234 past entry port 208 when caught at entry port 208, or the clinician must reposition one or more of guidewire 240, medical device 234, or catheter 202 and again attempt to advance medical device past entry port 208. To reduce catching of medical device 234 on entry port 208, a flaring device may be used to modify entry port 208, e.g., flare entry port 208, to better match an outer diameter of elongate body 206 to an inner diameter of catheter 204.

Figure 3B:
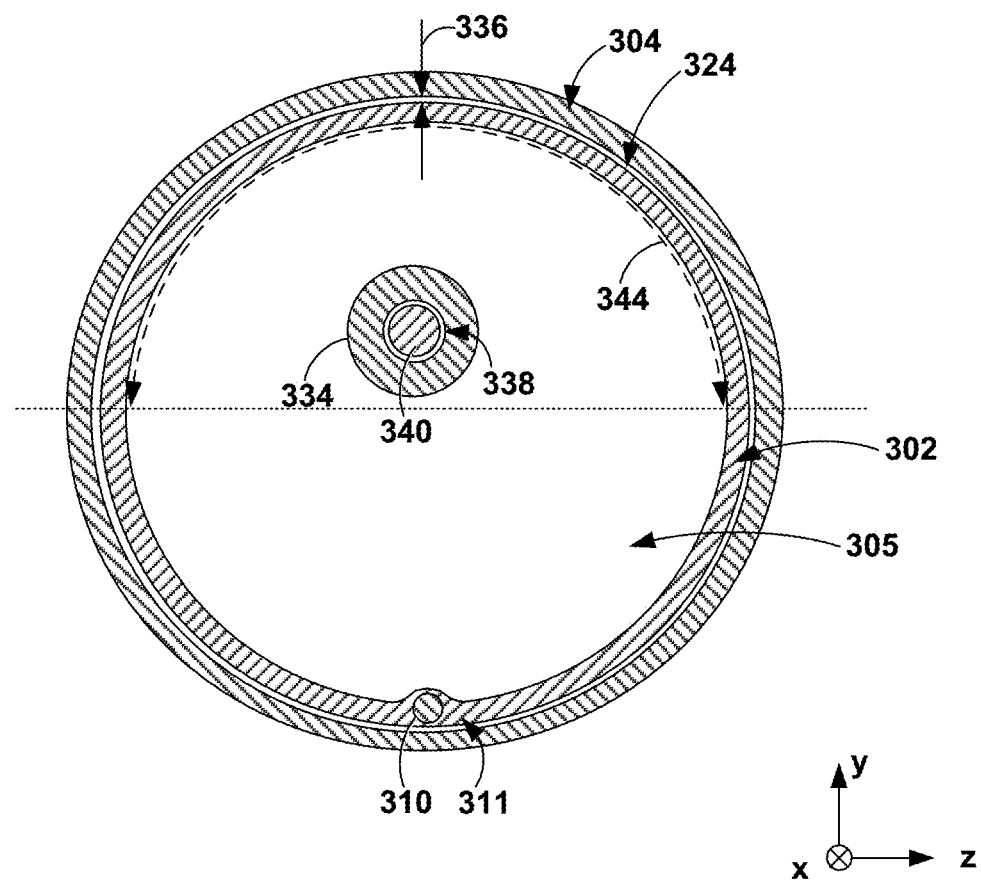
FIG. 3B is a conceptual transverse cross-sectional view of the example medical device system illustrated in FIG. 3B taken along line 3B-3B in FIG. 3A.

FIG. 3A is a conceptual longitudinal cross-sectional view of an example medical device system 300 illustrating a flared entry port 308 of a modified catheter 302 positioned within a lumen 324 of an outer catheter 304 and into which a medical device 334 is being inserted. FIG. 3B is a conceptual transverse cross-sectional view of the example medical device system 300 illustrated in FIG. 3A taken along line 3B-3B in FIG. 3A. Catheter 302 and outer catheter 304 may be the same as or substantially similar to catheter 202 and outer catheter 204, respectively, as discussed above in reference to FIGS. 2A and 2B, except for the differences described herein. For example, catheter 302 includes a push assembly 310 and an elongate body 306. Elongate body 306 extends along a longitudinal axis and defines a lumen 305 and an entry port 308 into the lumen 305. Entry port 308 extends from proximal end 330 to distal end 332 along a length of elongate body 306. Outer catheter 304 defines a lumen 324 through which catheter 302 may pass. Medical device 334 may pass from lumen 324 of outer catheter 304 into lumen 305 of catheter 302 by advancing medical device 334 over guidewire 340 that extends through lumen 338 of medical device 334.

As illustrated in FIG. 3A, entry port 308 defines a lip 328. Lip 328 is configured to reduce a mismatch between catheter 302 and outer catheter 304 (e.g., mismatch 236 discussed above in reference to FIGS. 2A and 2B). In some examples, an angle θ of lip 328 relative to longitudinal axis X of catheter 302 may be greater than 0-degree to about 60-degrees, such as greater than about 0-degree to about 45-degrees. Lip 328 may include (or define) at least one of a selected orientation relative to entry port 308, a selected cross-sectional dimension (e.g., diameter or length), a selected length L from entry port 308 to a non-flared portion 342 of elongate body 306 of catheter 302, or an arc that subtends a selected angle of the outer perimeter of entry port 308. By flaring entry port 308, an outer perimeter of catheter 302 may better correspond to an inner diameter of a second catheter 304 (referred to herein as an outer catheter) for example, compared to an unflared catheter.

In some examples, lip 328 may be asymmetrical relative to longitudinal axis X. For example, the orientation of lip 328 may extend predominately in the y-direction (orthogonal x-y axes are shown in FIG. 3A and the other figures for ease of description only and do not impart any specific intended direction of use). In other words, lip 328 may extend in a radial direction away from a nominal plane elongate body 106 (e.g., a plane of elongate body 106 extending parallel to the x-axis before flaring entry port 308), with a more predominate flaring the in y-direction. In other examples, lip 328 may be oriented in any suitable direction. For example, only one longitudinal half of entry port 308 may extend radially away from central longitudinal axis X to define lip 328. In some examples, a feature of catheter 302, such as, for example, push assembly 310, may reduce or prevent flaring of entry port 308 at the circumferential portion 311 of elongate body 306 directly adjacent push assembly 310. For example, a rigidity of push assembly 310, e.g., relative to elongate body 306, may prevent elongate body 306 being flared in a radial direction.

In some examples, an outer cross-sectional dimension (e.g., diameter) of the flared entry port 308 is substantially similar to an inner cross-sectional dimension (e.g., diameter) of outer catheter 304. That is, entry port 308 including lip 328 may define an exterior surface of catheter 302 that substantially matches (e.g., matches or nearly matches) the inner diameter of outer catheter 304. In this way, flared entry port 308 may help reduce or even eliminate GEC mismatch and the resulting free space between elongate body 306 and an interior of outer catheter 304 that may cause a medical device to get caught up on a leading edge of entry port 308. Additionally, or alternatively, flared entry port 308 may facilitate the introduction of medical devices into lumen 305 of catheter 302 without adversely impacting the navigability of catheter 302 through vasculature of a patient.

In some examples, the length L of lip 328 in a direction parallel to longitudinal axis X may be about 3 millimeters (mm) to about 5 mm. In some examples, the length L of lip 328 may be selected to provide a selected flexibility of lip 328. For example, a lip having a relatively shorter length L of may be less flexible than a lip having a relatively longer length L. In some examples, a more flexible lip 328 may enable a dimension of lip 328 to be equal to or greater than an inner dimension of outer catheter 304. For example, lip 328 may flex to match a dimension or shape of an inner surface of outer catheter 304 when positioned within lumen 324.

In some examples, lip 328 extends along an arc 344 that subtends any suitable angle of the outer perimeter of entry port 308. For example, as illustrated in FIG. 3B, arc subtends an angle of about 180-degrees. In other examples, the angle may be between about 45-degrees and about 360-degrees, such as about 45-degrees to about 315-degrees.

In some examples, lip 328 may reduce mismatch 336 to less than about 2 mm, such as less than about 0.5 mm, compared to a mismatch without lip 326 (e.g., mismatch 236). By reducing a size of mismatch 336, medical device 334 may be guided from lumen 324 of outer catheter 304 into lumen 305 of catheter 302 with a lower possibility of catching on entry port 308 or otherwise interfering with a trajectory of medical device 334 as it is advanced into outer catheter lumen 305.

Figure 4:
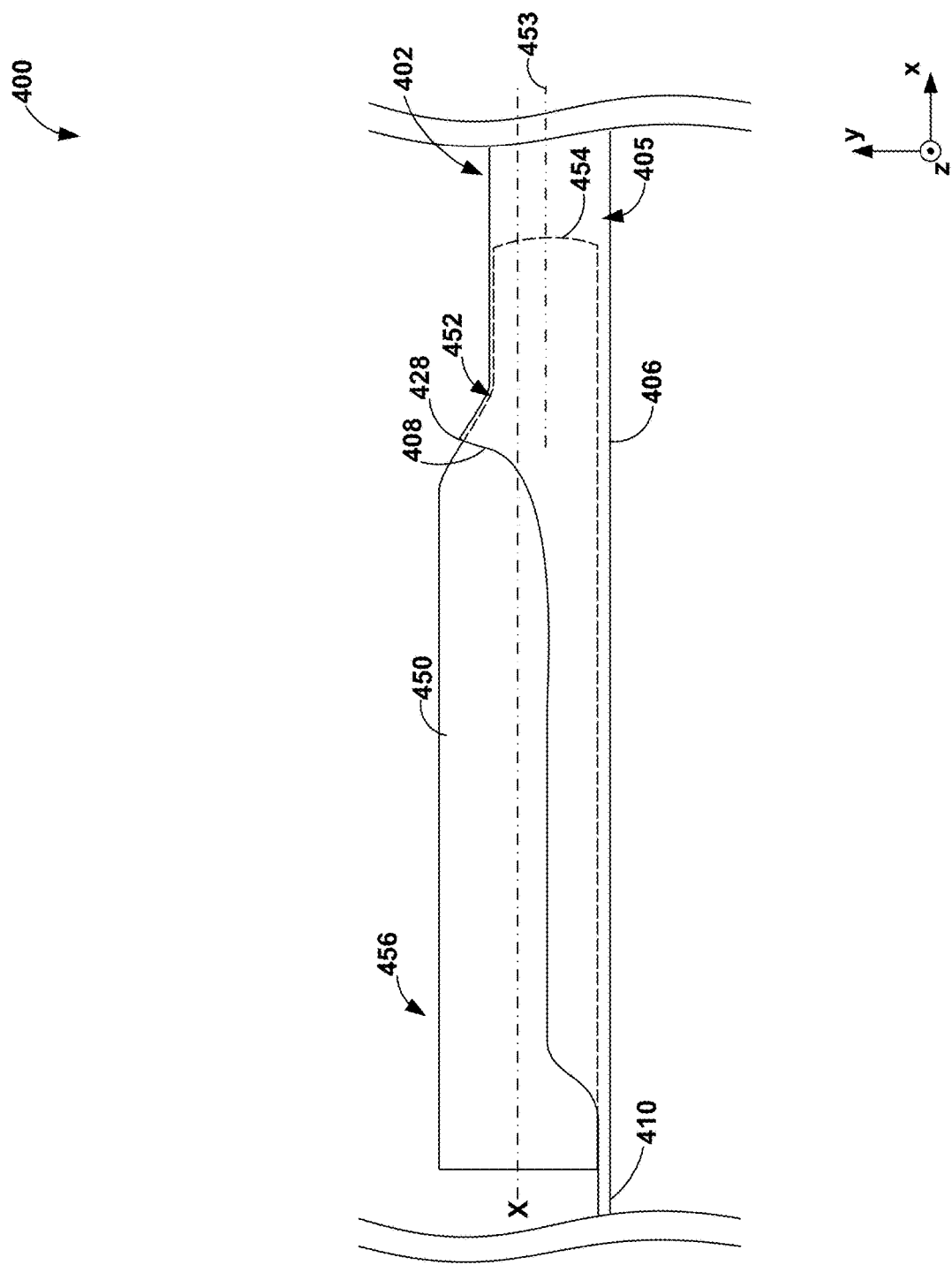
FIG. 4 is a conceptual side view of an example medical device system that includes a flaring pin and a catheter.
Figure 5:
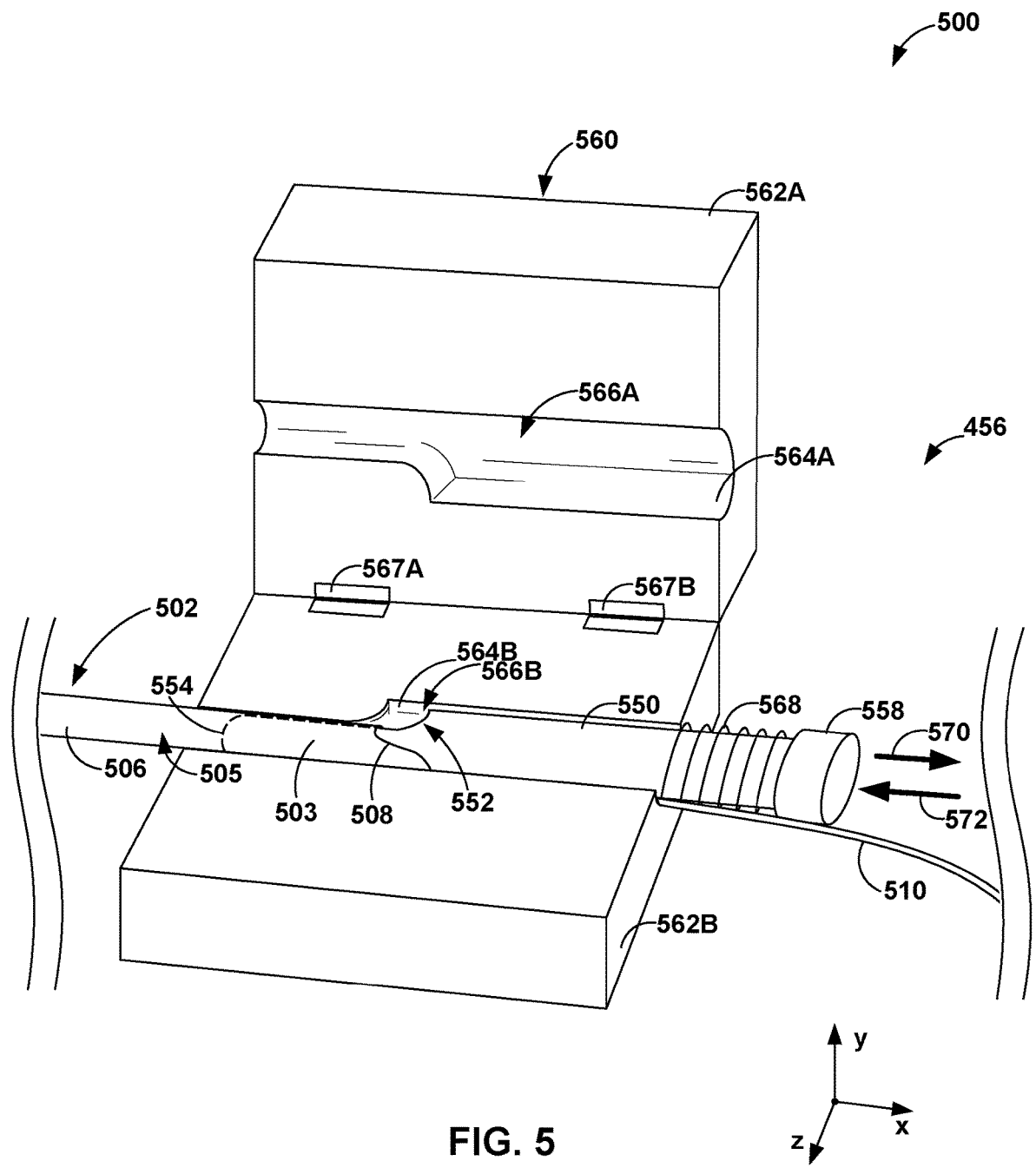
FIG. 5 is a conceptual plan view of an example medical device system that includes a catheter and a catheter flaring device comprising a housing and a flaring pin.

FIGS. 4 and 5, discussed in detail below, illustrate example devices configured to flare an entry port of a catheter, referred to herein as flaring devices. In some examples, the described flaring devices may include a plurality of flaring devices, each flaring device configured to be used with a selected catheter size and/or produce a selected flaring. For example, a first flaring device may be used with a 7 Fr catheter to flare the entry port to substantially correspond to 8 Fr, and a second flaring device may be used with a 5 Fr catheter and configured to flare the entry port to substantially correspond to 7 Fr. In this way, a clinician may selected a flaring device corresponding to a selected catheter size and a selected flare size.

FIG. 4 is a conceptual side view of an example flaring pin 450 ("pin 450") and a catheter 402. Pin 450 is configured to be advanced into an entry port 408 of catheter 402 to form a lip 428. For example, advancing flaring pin 450 into entry port 408 may increase a cross-sectional dimension of entry port 408. Catheter 402 may be the same as or substantially similar to catheter 302 as discussed above in reference to FIGS. 3A and 3B. For example, catheter 402 includes a push assembly 410 and an elongate body 406. Elongate body 406 extends along a longitudinal axis and defines a lumen 405 terminating in entry port 408. In some examples, medical device system 400 may include an outer catheter (e.g., outer catheter 304) and/or a medical device (e.g., medical device 334).

Pin 450 may be formed from any suitable material having a suitable durometer to deform entry port 408 of catheter 402 to define lip 428. In some examples, pin 450 may include a metal, such as, but not limited to, stainless steel, titanium, or any combination thereof. In some examples, pin 450 may include a relatively rigid plastic (e.g., more rigid than elongate body 406 of catheter 402), such as, but not limited to, an epoxy, high-density polyethylene, polyvinyl chloride, polycarbonate, acrylic, or any combination thereof. In some examples, pin 450 may include a metal and a plastic.

In some examples, pin 450 is configured to flare a selected outer perimeter (e.g., only part of the outer perimeter) of entry port 408 of catheter 402. For example, a distal portion 452 of pin 450 may define a conical shape. As one example, a distal end 454 of pin 450 may have a cross-sectional dimension (e.g., diameter) smaller than that of a non-flared configuration of entry port 408. In this way, distal end 454 may be inserted, e.g., by a clinician, into lumen 405 of elongate body 406 via entry port 408. Pin 450 may taper from a first cross-sectional dimension at a proximal portion 456 of pin 450 to a second cross-sectional dimension smaller than the first cross-sectional dimension at distal end 454. The taper may be substantially constant, vary in degree of taper (e.g., increasing or decreasing degree of taper), be stepwise, or otherwise define a shape configured to deform at least a portion of entry port 408 to define a selected shape of lip 428.

In some examples, distal portion 452 of pin 450 may define a conical shape that has a center axis 453 that is off-center relative to central longitudinal axis X. As a result of being off-center, pin 450 may cause lip 428 to be asymmetrical relative to longitudinal axis X. For example, lip 428 may extend radially away from central longitudinal axis X more predominately in the y-direction or only one longitudinal half of entry port 408 may flare radially outward. In this way, pin 450 may be configured to flare entry port 408 in a selected direction, rather than radially outwardly in all directions about central longitudinal axis X.

In some examples, pin 450 may be configured to flare entry port 408 by cold flaring, e.g., without application of heat to catheter 102. In some examples, pin 450 may include a heating element (not shown). An example heating element may include, for example, a resistive metal coil extending through a portion of the interior of pin 450 and coupled to an electrical power source. When an electrical current is applied to the metal coil, a temperature of the metal coil may increase and, thereby, heat pin 450 to a selected temperature. The temperature may be selected to soften and/or at least partially melt a material of elongate body 406 of catheter 402. In some examples, heat may be applied by a heating element that is not located within pin 450, for example, the heating element may be located in a housing configured to surround at least a portion of catheter 402 (e.g., housing portions 562 described with reference to FIG. 5). By softening and/or at least partially melting the material of elongate body 406 of catheter, pin 450 may more easily deform entry port 408 to define lip 428. In some examples, once cooled, elongate body 406 may better retain the selected shape of lip 428, compared to a pin 450 without a heating element. In this way, a heating element may facilitate forming lip 428.

In some examples, flaring pin 450 may be configured to be directly manipulated by a clinician. For example, a clinician may push flaring pin 450 into entry port 408. In some examples, flaring pin 450 may be coupled to a housing, such that the housing may engage at least a portion of catheter 102 and a clinician may manipulate flaring pin 450 or a member coupled to flaring pin 450 to advanced flaring pin 450 into entry port 408.

FIG. 5 is a conceptual plan view of an example medical device system 500 that includes a catheter 502 and a catheter flaring device 560 having a housing that includes a first housing portion 562A and a second housing portion 562B (collectively, "housing portions 562") and a flaring pin 550 ("pin 550"). Although discussed in reference to FIG. 5 as including two housing portions, in other examples, catheter flaring device 560 may include a single, unitary housing. Catheter 502 and pin 550 may be the same as or substantially similar to catheter 402 and pin 450, respectively, discussed above in reference to FIG. 4, except for the differences described herein. For example, catheter 502 includes a push assembly 510 and an elongate body 506 that terminates in an entry port 508. Pin 550 includes a distal portion 552 that is configured to flare a selected outer perimeter of entry port 508 of catheter 502.

In some examples, housing portions 562 are configured to engage an exterior surface 503 of catheter 502 proximate entry port 508. For example, housing portions 562 may include respective interior surfaces 564A and 564B (collectively, "interior surfaces 564") that define respective cavities 566A and 566B (collectively, "cavities 566"). Cavities 566 may be configured to receive at least a portion of catheter 502 including entry port 508. For example, housing portions 562 may be coupled by hinges 567A and 567B such that housing portions 562 may be moveable between an open configuration to receive catheter 502, as illustrated in FIG. 5, and a closed position in which both housing portions 562 engage catheter 502. In this way, first housing portion 562A and second housing portion 562B are configured to move relative to each other to enclose at least a portion of catheter 502.

In some examples, a shape of interior surfaces 564 of housing portions 562 may be configured to orient entry port 508 of catheter 502 in a selected orientation relative to pin 550. For example, interior surfaces 564 may include one or more protrusions or depressions that correspond to features of catheter 502, such as entry port 508 or push assembly 510, such that catheter 502 is received within cavities 566 in a predetermined orientation. In this way, housing portions 562 may be configured to receive catheter 502 in a predefined orientation relative to pin 550 and help prevent a clinician from inadvertently inserting catheter 502 in housing portions 562 in an unintended orientation.

In some examples, cavities 566 may be shaped to correspond to the selected flared shape of entry port 508. For example, cavities 566 may define a selected shape of an outer perimeter of elongate body 506 after entry port 508 has been flared. In this way, housing portions 562 may be used to control a flaring of entry port 508, for example, to prevent pin 550 from being pushed too far into lumen 505, which may define a lip having too long of a length (measured along a longitudinal axis of catheter 502). As another, housing portions 562 defining a pre-shaped cavities 566 corresponding to a desired amount of flaring of entry port 508 may help ensure entry port 508 is sufficiently flared by providing tactile feedback to the clinician. The tactile feedback may, for example, be in the form of the clinician being unable to push pin 550 further into housing portions 562.

In some examples, pin 550 may be mechanically coupled to housing portions 562 and may be configured to travel along a predetermined direction, e.g., a linear direction. For example, pin 550 may travel in one or more grooves, along one or more rails, or similar structures extending parallel to the x-axis and defined by interior surface 564B of first housing portion 562A. In this way, second housing portion 562B may be mechanically coupled to pin 550 in sliding engagement. By mechanically coupling to second housing portion 562B in sliding engagement, pin 550 may be movable between a first position in which housing portions 562 are configured to receive catheter 502 in cavity 566B, e.g., indicated by arrow 570, and a second position in which pin 550 is positioned relative to catheter 502 receive in housing portions 562 to flare entry port 508 of catheter 502, e.g., indicated by arrow 572.

In some examples, after catheter 502 is positioned within cavity 566B, and before pin 550 is advanced into entry port 508, a clinician may move housing portions 562 into the closed configuration to enclose and engage at least a portion of catheter 502 including entry port 508. For example, moving housing portions 562 into the closed configuration may engage catheter 502 by friction fit between at least a portion of interior surfaces 564 and at least a portion of elongate body 506 to help hold catheter 502 in place relative to housing portions 562. In this way, interior surfaces 564 of housing portions 562 are configured to engage an exterior surface of catheter 502 proximate entry port 508 such that pin 550 may be advanced into lumen 505 via entry port 508 to increase a cross-sectional dimension of entry port 508.

In some examples, catheter flaring device 560, e.g., pin 550, may include a button 558, or other bulbous structure, to facilitate advancement of pin 550 into lumen 505 of catheter 502. For example, a clinician may apply a push force to button 558 to advance pin 550 in the direction indicated by arrow 572. Button 558 may enable a clinician to apply a greater or a more consistent push force to pin 550 to advance pin 550 into lumen 505 via entry port 508 without button 558 and spring 568. For example, button 558 may provide a structure for the clinician to grasp, and may also act as a stop to prevent advancement of pin 550 into lumen 505 of catheter 502 past a desired point, which may result in a lip having a longer than desired a length.

In some examples, catheter flaring device 560 may include a depression-return device 568. Depression-return device 568 may be configured to, upon release of the push force to advance pin 550 into entry port 508 of catheter 502, return pin 550 to a home position. For example, depression-return device 568 may apply a force to pin 550 in the direction indicated by arrow 570. As illustrated in FIG. 5, depression-return device 568 includes a coil spring. In other examples, depression-return device 568 may include one or more different mechanical springs or pneumatic cylinders.

Figure 6A:
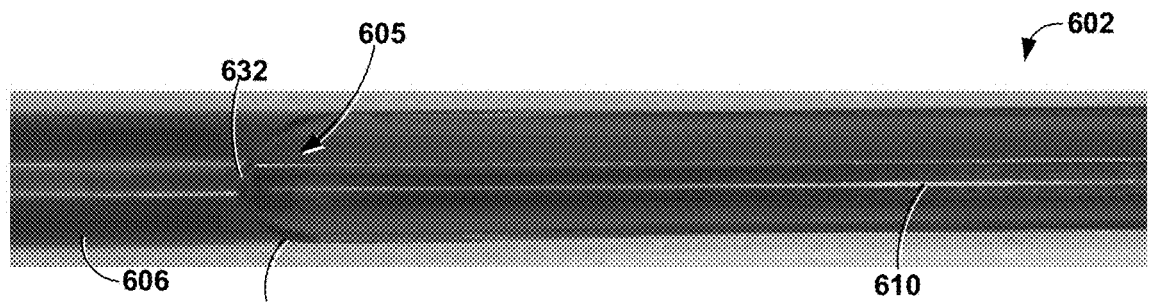
FIGS. 6A and 6B are photographs illustrating a top view and a side view of an example catheter before flaring an entry port.
Figure 6B:
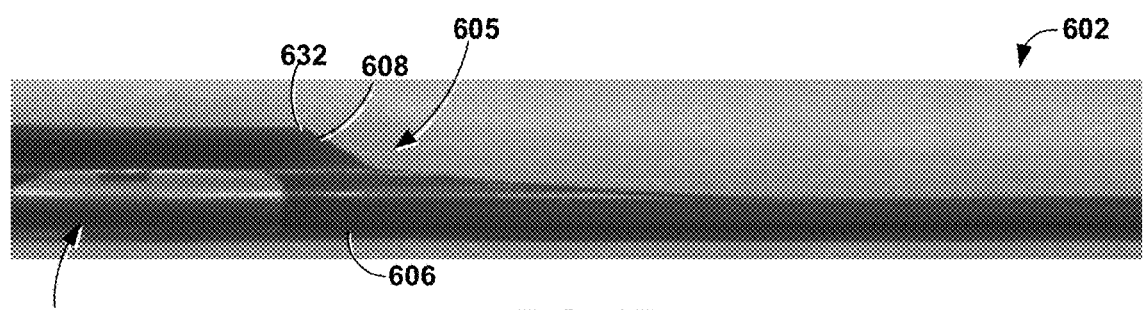
Figure 6C:
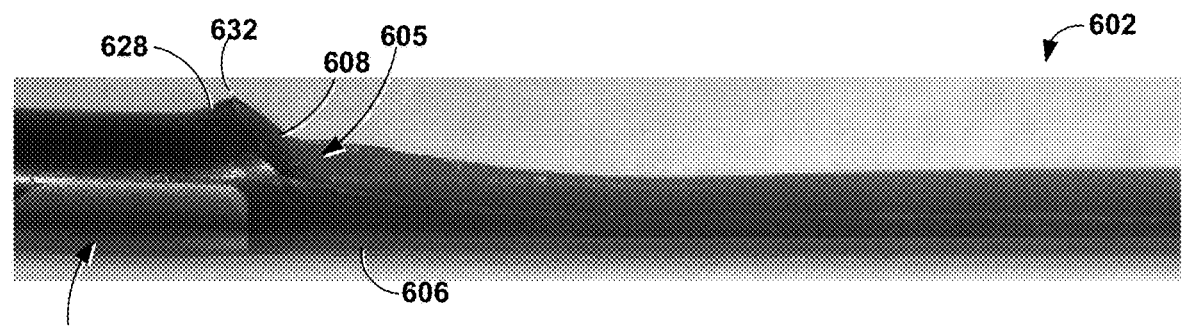
FIGS. 6C and 6D are photographs illustrating an elevated view and a side view of the catheter after flaring the entry port.
Figure 6D:
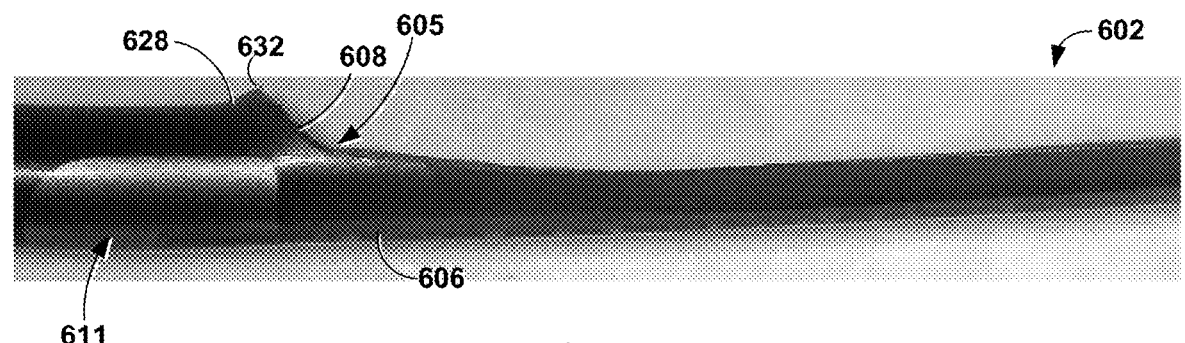

FIGS. 6A and 6B are photographs illustrating a top view and side view of an example catheter 602 before flaring an entry port 608, and FIGS. 6C and 6D are photographs illustrating an elevated view and side view of catheter 602 after flaring entry port 608. Catheter 602 may be the same as or substantially similar to catheters 102, 202, 302, 402, and 502 discussed above in reference to FIGS. 1-5, except for the differences described herein. For example, catheter 602 includes a push assembly 610 having an anchor member 611 coupled to an elongate body 606. Elongate body 606 may extend along a longitudinal axis and define a lumen 605 terminating in entry port 608. Entry port 608 extends from proximal end (not shown) to distal end 632 along a length of elongate body 606.

As illustrated in FIGS. 6A and 6B, prior to flaring entry port 608, entry port 608 does not include a lip. In examples in which catheter 602 is a guide extension catheter, catheter 202 may define a mismatch with a guide catheter (not shown). Similar to the discussion above in reference to FIGS. 2A and 2B, in some cases, the mismatch may be from about 0.33 mm to about 2 mm, such as about 0.5 mm to about 1 mm. To reduce catching of a medical device on entry port 608, a flaring device, such as catheter flaring device 560, may be used to modify entry port 608, e.g., flare entry port 608, to better match an outer diameter of elongate body 606 to an inner diameter of a second catheter, such as a guide catheter.

As illustrated in FIGS. 6C and 6D, after flaring entry port 608, such as, for example, using a catheter flaring device 560, entry port 608 defines a lip 628. Similar to the discussion above in reference to FIGS. 3A and 3B, lip 628 is configured to reduce the mismatch between catheter 602 and, for example, an inner diameter of a guide catheter. Lip 628 may include at least one of a selected orientation relative to entry port 608, a selected cross-sectional dimension (e.g., diameter or length), a selected length L from entry port 608 to a non-flared portion of elongate body 606 of catheter 602, or an arc that subtends selected angle of the outer perimeter of entry port 608. By flaring entry port 608, an outer perimeter of catheter 602 may better correspond to an inner diameter of a second catheter, for example, compared to an unflared catheter.

Figure 7:
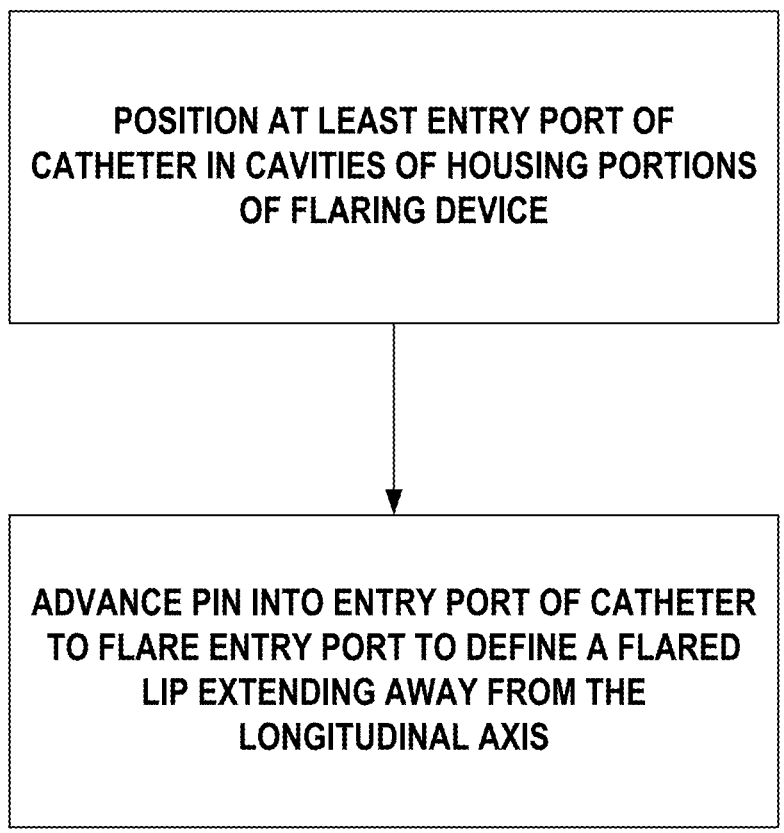
FIG. 7 is a flow diagram illustrating an example technique of modifying an entry port of a catheter.

The medical device systems described herein may be used to flare an entry port of a catheter, such as a guide extension catheter. FIG. 7 is a flow diagram illustrating an example technique of modifying an entry port of a catheter. Although the technique illustrated in FIG. 7 is described in reference to medical device system 500 described above in reference to FIG. 5, the technique may be used with other medical device systems, such as one or more of medical device systems 100, 200, 300, or 400.

The technique illustrated in FIG. 7 includes positioning at least entry port 508 of catheter 502 in cavities 566 of housing portions 562 of flaring device 560. As discussed above, catheter 502 may include elongate body 506 extending along a longitudinal axis and defining lumen 505 terminating in entry port 508. Also, as discussed above, flaring device 560 may include housing portions 562 and pin 550. Housing portions 562 may include interior surfaces 564 defining cavities 566 that are shaped to receive the portion of catheter 602. Interior surfaces 564 of housing portions 562 may be configured to engage exterior surface 503 of catheter 502 proximate entry port 508.

The technique illustrated in FIG. 7 also includes advancing pin 550 into lumen 505 via entry port 508 of catheter 502 to flare entry port 508. Flared entry port 508 may define a flared lip (e.g., flared lip 428) extending away from a central longitudinal axis X of elongate body 506. In examples in which a shape of interior surfaces 564 of housing portions 562 corresponds to a selected flare-shape of entry port 508 of catheter 502, advancing pin 550 may include advancing pin 550 until the flared lip contacts interior surfaces 564 of housing portions 562. In this way, interior surfaces 564 may include a positive stop that prevents over-flaring of entry port 508.

In examples in which flaring device 560 further includes a depression-return device 568, the technique may include, after advancing pin 550, releasing a force applied to advance pin 550 into lumen 505 via entry port 508 of catheter 502. In some examples, depression-return device 568, after releasing the force, may automatically return pin 550 to a home position. The home position may include a position of pin 550 such that pin 550 does not extend into lumen 505 via entry port 508. By automatically returning pin 550 to a home position, a clinician may not need to manually return pin 550 to the home position.

In examples in which flaring device 560 includes a heating element configured to at least soften a material of catheter 502, the technique may include applying, by the heating element, heat to at least the portion of the catheter. Heating at least a portion of catheter 502 may reduce an amount of force necessary to flare entry port 508.

A clinician may modify the entry port 508 of catheter 502 using the technique described with reference to FIG. 7 or using other devices and techniques described herein at any suitable time, such as in a clinic (e.g., a cath-lab) prior to or during a medical procedure.

The following clauses illustrate example subject matter described herein.

Clause 1. A device comprising: a housing comprising an interior surface defining a cavity configured to receive at least a portion of a catheter having an entry port, wherein the interior surface of the housing is configured to engage an exterior surface of the catheter proximate the entry port; and a pin configured to be advanced into the entry port of the catheter while at least the portion of the catheter is positioned in the cavity to increase a cross-sectional dimension of the entry port.

Clause 2. The device of clause 1, wherein the pin is configured to flare at least part of the entry port of the catheter.

Clause 3. The device of clause 1 or 2, wherein a distal portion of the pin defines a conical shape.

Clause 4. The device of any one of clauses 1 through 3, wherein a distal portion of the pin defines a conical shape that is off-center relative to a central longitudinal axis of a proximal portion of the pin.

Clause 5. The device of any one of clauses 1 through 4, wherein the pin is mechanically coupled to the housing in sliding engagement.

Clause 6. The device of any one of clauses 1 through 5, further comprising a depression-return device configured to, upon release of a force to advance the pin into the entry port of the catheter, return the pin to a home position.

Clause 7. The device of clause 6, wherein the depression-return device comprises a spring or a pneumatic cylinder.

Clause 8. The device of any one of clauses 1 through 7, further comprising a heating element configured to soften a material of the catheter.

Clause 9. The device of any one of clauses 1 through 8, wherein the shape of the interior surface of the housing corresponds to a selected flare-shape of the entry port of the catheter.

Clause 10. The device of any one of clauses 1 through 9, wherein the shape of the interior surface of the housing is configured to orient the entry port of the catheter in a selected orientation relative to the pin.

Clause 11. The device of any one of clauses 1 through 10, wherein the housing comprises a first portion and a second portion mechanically coupled to the first portion by one or more hinges, wherein the first portion and the second portion are configured to move relative to each other to enclose at least the portion of the catheter.

Clause 12. A medical device system comprising: a catheter comprising an elongate body extending along a central longitudinal axis and defining a lumen terminating in an entry port; and a flaring device comprising: a housing comprising an interior surface defining a cavity shaped to receive at least a portion of the catheter, wherein the interior surface of the housing is configured to engage an exterior surface of the catheter proximate the entry port; and a pin configured to be advanced into the entry port of the catheter while at least the portion of the catheter is positioned in the cavity to flare the entry port to define a flared lip extending away from the central longitudinal axis.

Clause 13. The medical device system of clause 12, wherein the flared lip of the entry port tapers towards the central longitudinal axis in a distal direction.

Clause 14. The medical device system of clause 12 or 13, wherein the flared lip is asymmetrical relative to the central longitudinal axis.

Clause 15. The medical device system of any one of clauses 12 through 14, wherein an angle of the flared lip relative to the central longitudinal axis is greater than 0-degrees to about 45-degrees.

Clause 16. The medical device system of any one of clauses 12 through 15, wherein a length of the flared lip in a direction parallel to the central longitudinal axis is about 3 millimeters to about 5 millimeters.

Clause 17. The medical device system of any one of clauses 12 through 16, wherein an outer perimeter of the flared lip subtends an angle from about 45-degree to about 315-degrees.

Clause 18. The medical device system of any one of clauses 12 through 17, wherein the catheter is a guide extension catheter comprising the elongate body and a push assembly including an elongate member and an anchor member, wherein a maximum cross-sectional dimension of the elongate member is less than a cross-sectional dimension of the entry port, wherein the anchor member is positioned at a distal end of the elongate member and fixed to the elongate body proximate the entry port.

Clause 19. The medical device system of any one of clauses 12 through 18, wherein the pin defines a conical shape having a central axis that is off-center relative to the central longitudinal axis of the catheter when at least the portion of the catheter is positioned in the cavity.

Clause 20. The medical device system of any one of clauses 12 through 19, wherein the pin is mechanically coupled to the housing in sliding engagement.

Clause 21. The medical device system of any one of clauses 12 through 20, wherein the flaring device further comprises a depression-return device configured to, upon release of a force to advance the pin into the entry port of the catheter, automatically return the pin to a home position.

Clause 22. The medical device system of claim 21, wherein the depression-return device comprises a spring or a pneumatic cylinder.

Clause 23. The medical device system of any one of clauses 12 through 22, wherein the flaring device further comprises a heating element configured to at least soften a material of the catheter.

Clause 24. The medical device system of any one of clauses 12 through 23, wherein the shape of the interior surface of the housing corresponds to a selected flare-shape of the entry port of the catheter.

Clause 25. The flaring device of any one of clauses 12 through 24, wherein the shape of the interior surface of the housing is configured to orient the entry port of the catheter in a selected orientation relative to the pin.

Clause 26. A method comprising: positioning at least an entry port of a catheter in a cavity of a housing of a flaring device, wherein the catheter comprises an elongate body extending along a central longitudinal axis and defining a lumen terminating in the entry port, and wherein the flaring device comprises: the housing comprising an interior surface defining the cavity shaped to receive at least a portion of the catheter comprising the entry port, wherein the interior surface of the housing is configured to engage an exterior surface of the catheter proximate the entry port; and a pin; and while at least the entry port of the catheter is positioned in the cavity of the housing, advancing the pin into the entry port of the catheter to flare the entry port to increase a cross-sectional dimension of the entry port.

Clause 27. The method of clause 26, wherein advancing the pin into the entry port of the catheter increases the cross-sectional dimension of the entry port by at least flaring a lip of the catheter.

Clause 28. The method of clause 26 or 27, wherein advancing the pin comprises advancing the pin until the entry port contacts the interior surface of the housing.

Clause 29. The method of any one of clauses 26 through 28, wherein the flaring device further comprises a depression-return device, wherein the method further comprises, after advancing the pin, releasing a force applied to advance the pin into the entry port of the catheter, wherein the depression-return device, after releasing the force, automatically returns the pin to a home position.

Clause 30. The method of any one of clauses 26 through 29, wherein the flaring device further comprises a heating element configured to at least soften a material of the catheter, wherein the method further comprises applying, by the heating element, heat to at least the portion of the catheter.

Clause 31. The method of any one of clauses 26 through 30, further comprising selecting the flaring device based on a desired flare-shape of the entry port of the catheter.

Various examples have been described. These and other examples are within the scope of the following claims.

What is claimed is:

1. A kit comprising:
  a plurality of flaring devices, each flaring device of the plurality of flaring devices comprising:
    a housing comprising an interior surface defining a cavity configured to receive at least a portion of a catheter having an entry port, wherein the interior surface of the housing is configured to engage an exterior surface of the catheter proximate the entry port; and
    a pin comprising a proximal portion and a distal portion, wherein the pin is configured to be advanced into the cavity while at least the portion of the catheter is positioned in the cavity to increase a cross-sectional dimension of the entry port,
    wherein the pin defines a taper between a first cross-sectional dimension of the proximal portion and a second cross-sectional dimension of the distal portion,
    wherein the proximal portion defines a first central longitudinal axis and the distal portion defines a second central longitudinal axis offset from the first central longitudinal axis,
  wherein each flaring device of the plurality of flaring devices is configured to be used with a different catheter diameter or produce a different flare size of the catheter, and
  wherein each flaring device of the plurality of flaring devices further comprises a depression-return device configured to, upon release of a force to advance the pin from a home position into the cavity, return the pin to the home position.

2. The kit of claim 1, wherein each pin is configured to flare at least part of the entry port of the catheter.

3. The kit of claim 1, wherein the distal portion of each pin defines a conical shape.

4. The kit of claim 1, wherein each pin is mechanically coupled to the housing of the respective flaring device in sliding engagement.

5. The kit of claim 1, wherein each flaring device further comprises a heating element configured to soften a material of the catheter.

6. The kit of claim 1, wherein the shape of the interior surface of each housing corresponds to a selected flare-shape of the entry port of the catheter.

7. The kit of claim 1, wherein the shape of the interior surface of each housing is configured to orient the entry port of the catheter in a selected orientation relative to the pin.

8. The kit of claim 1, wherein each housing comprises a first portion and a second portion mechanically coupled to the first portion by one or more hinges, wherein the first portion and the second portion are configured to move relative to each other to enclose at least the portion of the catheter.

9. A medical device system comprising:
the kit of claim 1; and
the catheter comprising an elongate body extending along a central catheter longitudinal axis and defining a lumen terminating in the entry port,
wherein each pin is configured to be advanced into the entry port of the catheter while at least the portion of the catheter is positioned in the respective cavity to flare the entry port to define a flared lip extending away from the central catheter longitudinal axis.

10. The medical device system of claim 9, wherein the flared lip of the entry port tapers towards the central catheter longitudinal axis in a distal direction.

11. The medical device system of claim 9, wherein the flared lip is asymmetrical relative to the central catheter longitudinal axis.

12. The medical device system of claim 9, wherein an angle of the flared lip relative to the central catheter longitudinal axis is greater than 0-degrees to about 45-degrees.

13. The medical device system of claim 9, wherein a length of the flared lip in a direction parallel to the central catheter longitudinal axis is about 3 millimeters to about 5 millimeters.

14. The medical device system of claim 9, wherein an outer perimeter of the flared lip subtends an angle from about 45-degree to about 315-degrees.

15. The medical device system of claim 9, wherein the catheter is a guide extension catheter comprising the elongate body and a push assembly including an elongate member and an anchor member, wherein a maximum cross-sectional dimension of the elongate member is less than a cross-sectional dimension of the entry port, wherein the anchor member is positioned at a distal end of the elongate member and fixed to the elongate body proximate the entry port.

16. The medical device system of claim 9, wherein each pin is mechanically coupled to the housing in sliding engagement.

17. The kit of claim 1, wherein each depression-return device comprises a spring or a pneumatic cylinder.

18. The kit of claim 1, wherein each pin is configured to increase the cross-sectional dimension of the entry port without an application of heat to the catheter.

19. The kit of claim 1, wherein each depression return device is positioned between an end of the pin and an outer surface of the housing.

20. A method comprising:
selecting, from a plurality of flaring devices, a flaring device, wherein each flaring device of the plurality of flaring device comprises:
a housing comprising an interior surface defining a cavity configured to receive at least a portion of a catheter comprising an entry port, wherein the interior surface of the housing is configured to engage an exterior surface of the catheter proximate the entry port; and
a pin comprising a proximal portion and a distal portion, wherein the pin is configured to be advanced into the cavity while at least the portion of the catheter is positioned in the cavity to increase a cross-sectional dimension of the entry port,
wherein the pin defines a taper between a first cross-sectional dimension of the proximal portion and a second cross-sectional dimension of the distal portion,
wherein the proximal portion defines a first central longitudinal axis and the distal portion defines a second central longitudinal axis offset from the first central longitudinal axis; and
a depression-return device configured to, upon release of a force to advance the pin from a home position into the cavity, return the pin to the home position,
wherein each flaring device of the plurality of flaring devices is configured to be used with a different catheter diameter or produce a different flare size of the catheter;
positioning at least the entry port of the catheter in the cavity of the housing of the flaring device; and
while at least the entry port of the catheter is positioned in the cavity of the housing, advancing the pin into the entry port of the catheter to flare the entry port to increase a cross-sectional dimension of the entry port, wherein advancing the pin into the entry port comprises applying the first force to the pin to move the pin from the first position to the second position.

21. The method of claim 20, wherein advancing the pin into the entry port of the catheter increases the cross-sectional dimension of the entry port by at least flaring a lip of the catheter.

22. The method of claim 20, wherein advancing the pin comprises advancing the pin until the entry port contacts the interior surface of the housing.

\* \* \* \* \*